United States Patent [19]

Prosl et al.

[11] Patent Number: 4,569,675
[45] Date of Patent: Feb. 11, 1986

[54] TRANSCUTANEOUS INFUSION SYSTEM

[75] Inventors: Frank R. Prosl, Duxbury; Joseph J. Szymanski, Walpole, both of Mass.

[73] Assignee: Infusaid Corporation, Norwood, Mass.

[21] Appl. No.: 531,038

[22] Filed: Sep. 12, 1983

[51] Int. Cl.$^4$ ............................................. A61M 5/00
[52] U.S. Cl. .................................... 604/175; 604/280; 128/DIG. 26
[58] Field of Search ................ 604/175, 174, 179, 93, 604/280, 164, 283; 128/DIG. 26

[56] References Cited

U.S. PATENT DOCUMENTS

| | | | |
|---|---|---|---|
| 3,310,051 | 3/1967 | Schulte | 604/175 |
| 3,714,945 | 2/1973 | Stanley | 604/164 |
| 4,397,641 | 8/1983 | Jacobs | 128/DIG. 26 X |
| 4,400,169 | 8/1983 | Stephen | 604/175 X |
| 4,419,094 | 12/1983 | Pater | 604/180 X |
| 4,435,174 | 3/1984 | Redmund et al. | 604/174 |

Primary Examiner—Stephen O. Pellegrino
Attorney, Agent, or Firm—Cesari and McKenna

[57] ABSTRACT

A transcutaneous infusion system comprises an implantable infusate injection port for conducting infusate from the port to an infusion site in the body. The port is supplied with infusate through a penetrable septum located directly under the skin. To infuse the patient, a flexible injection cannula encircling a needle which is slightly longer than the cannula is inserted through the septum into the port and then the needle is withdrawn leaving the free end of the flexible cannula in the port. The opposite end of the cannula is provided with a fitting for connecting the cannula to the outlet of a fluid administration set. The system also includes a bracket removably connected to the cannula and taped to the patient adjacent the injection site so that the bracket anchors the cannula and its associated fittings and tubing against the patient's skin, while assuring that the cannula is not bent to an extent that will stop fluid flow into the port.

3 Claims, 3 Drawing Figures

TRANSCUTANEOUS INFUSION SYSTEM

This invention relates to a transcutaneous infusion system. It relates more particularly to such a system which facilitates the long-term infusion of fluid into a patient without undue patient discomfort.

BACKGROUND OF THE INVENTION

Some medical therapies require that a fluid be infused into a patient's blood circulatory system. Each such infusion may be brief or it may be prolonged depending upon the patient's medical problem. Thus, for example, while one patient may be required to receive an infusion for an hour each week for many months, another patient might require an infusion for a period of one week each month. These regimens might apply, for example, to patients receiving chemotherapy for treatment of cancer. In the most usual procedure, a cannula is inserted through the skin into a vein in the patient's arm or leg. The cannula is then connected by tubing to a supply of the infusate which is administered to the patient in the prescribed amount for the proper length of time. In some cases, however, particularly with older patients, it becomes difficult to repeatedly find accessible venous infusion sites.

Also, when infusing a drug into a patient's venous system, it is sometimes necessary to limit the concentration of the drug because the amount of blood available to mix with the drug is limited by the relatively small diameter of the vein and because blood moves rather slowly through the vein. Therefore, it takes longer for the drug to take effect.

To avoid the aforesaid problems with venous infusion, implantable infusate injection ports have been developed. The injection port includes a chamber within the device and a penetrable self-sealing septum. When the injection port is implanted, that septum is located directly under the skin. A small tube extends from the chamber to the particular infusion site. An example of such a surgical reservoir is disclosed in U.S. Pat. No. 3,310,051. Another such device is marketed by Infusaid Corporation, Sharon, Mass. under the trademark Infuse-A-Port.

Such an appliance, once installed, gives permanent access to a specific internal region of the body and serves as a continuously available conduit placed in the body but once. Thereafter, a hypodermic syringe or drug adminstration cannula need only be placed in fluid communication with the chamber to inject fluids under pressure into the affected interior region of the body. Since the chamber communicates directly with the infusion site, a drug can be administered in higher concentration without unduly adversely affecting the rest of the patient's body. If the chamber communicates with the carotid artery, for example, there is a relatively large volume of relatively fast flowing blood available to mix with the higher-concentration infusate.

When fluid is infused into a patient in the usual way using an injection needle or cannula, the needle can be inserted into a vein, for example, at an angle with respect to the skin surface so that the cannula lies more or less parallel to the vein. In that position, the needle can be taped to the patient's skin. Accordingly, it does not project out from the patient where it could become caught by bedding or clothing and cause discomfort to the patient or, in extreme cases, be pulled from the patient.

However, when a patient is fitted with an implantable infusate injection port, the injection needle must be inserted into the injection port's septum at more or less a right angle to the outlying skin surface. If the infusion is a prolonged one, the needle must remain projecting out of the patient's body in position to be snagged by clothing, bedding, etc. as the patient moves about in the bed or chair. The bending moments applied to the needle are transmitted to the injection port tending to cause tearing of the septum or cocking within the body resulting in patient pain or discomfort. Also, in extreme cases, the needle can be bent or broken by the sideways forces exerted upon it or be pulled out of the injection port causing the drug to be misdelivered to the subcutaneous tissue.

To avoid the aforesaid problems, it is current practice to inject infusate into such implantable injection ports using needles which are prebent more or less at a right angle so that, after insertion of the needle into the port, the needle lies more or less parallel to the patient's skin adjacent the injection site. Thus, it is in a position to be secured to the patient's skin with adhesive tape so that it no longer catches on bedding and clothing. The problem with this procedure, however, is that the distance from the surface of the patient's skin to the injection port varies from patient to patient and, even with a single patient over time as his weight varies. This means that the injection needle must be prebent to suit each patient prior to each injection if it is to penetrate sufficiently into the port and still lie against the skin of the patient. Accordingly, that solution to the needle projection problem is not entirely satisfactory.

SUMMARY OF THE INVENTION

The present invention aims to provide a transcutaneous infusion system which permits connection by way of an injection needle to an implantable infusate injection port so as to produce a minimum projection at the injection site.

Another object of the invention is to provide a system such as this which firmly anchors the injection needle to the patient's body adjacent to the injection site.

A further object of the invention is to provide a transcutaneous infusion system which allows a patient having a prolonged infusion to be disconnected from and reconnected to the infusate source for brief periods without adverse consequences to the patient.

Still another object of the invention is to provide a transcutaneous infusion system which facilitates the prolonged infusion of a drug directly to a selected infusion site within the patient's body.

Other objects will, in part, be obvious and will, in part, appear hereinafter.

The invention accordingly comprises the features of construction, combination of elements and arrangement of parts which will be exemplified in the following detailed description, and the scope of the invention will be indicated in the claims.

Briefly the present system utilizes a known implantable infusate injection port, say, the one described above marketed by Infusaid Corporation. The injection port is arranged to be implanted in the patient's body so that the injection port's septum is located directly under the skin of the patient in position to receive an injection needle. A small flexible tube extending from the device leads to a selected infusion site in the patient's body, e.g. the tube end is sutured into the carotid artery. The system also includes a special injection set comprising a long needle surrounded by a thin-walled flexible resilient cannula terminated by a fitting adapted to be connected to a mating fitting at the end of the outlet tube on a fluid administration set.

The third component of the system is a small bracket which is used to shape the flexible injection cannula and hold the cannula against the patient after insertion into the injection port. This bracket comprises a fin having a pair of ears extending laterally from opposite sides of the fin. The fin is formed with a longitudinal passage extending adjacent the upper edge of the fin and the fin has a rounded nose portion with an edge groove aligned with that passage. The diameters of the passage and groove are sized to snugly receive the cannula. The cannula and bracket may be sold as a kit designed for use with the infusate injection port and may be discarded after each such use.

In describing the present system, it is assumed that the injection port portion of the system has been implanted in the patient in the customary way. When it is desired to infuse a drug into the patient by way of the injection port for a prolonged period, the injection needle and surrounding cannula are first threaded through the bracket passage. Then the shrouded needle is inserted through the patient's skin and the reservoir septum until the needle bottoms in the injection port. Then the needle is withdrawn leaving the flexible cannula projecting through the skin into the port.

The bracket is then positioned with its nose adjacent to the injection site and with its ears flush against the patient's skin so that the cannula engages in the rounded nose groove and makes a smooth transition from the point where it projects perpendicularly from the patient's skin to a horizontal disposition with its end fitting positioned against the patient's skin. Then the bracket ears are secured to the patient by adhesive strips. Finally, the cannula fitting is connected to a mating fitting leading from a conventional fluid administration set.

With this arrangement, the connections between the administration set and the injection port are all located right adjacent to the injection site and close to the patient's body so that they are in no position to be caught on or engaged by nearby objects such as bedding, clothing, etc. Consequently, the administration of infusate can proceed for a prolonged period without undue patient discomfort and without any likelihood of the injection cannula being pulled inadvertently from the reservoir because of being caught on nearby objects.

Further, as will be seen, the present system can be disconnected from the infusate supply for one reason or another without fear of the infusate path to the reservoir becoming unsterile or of passing air bubbles to the infusion site in the patient's body.

When injection of the infusate into the reservoir is completed, the bracket is detached from the patient's skin and the cannula tube withdrawn from the injection port septum which closes immediately, preventing escape of infusate from the port. The site of the injection through the patient's skin soon heals so that the same site is available when the next infusion procedure is required and the aforesaid process repeated.

Thus, the present transcutaneous infusion system greatly facilitates the introduction of infusate into an implanted infusate injection port and it assures that the transcutaneous connection to the port is compact and unobtrusive so that it does not interfere with the patient's movements or cause undue patient discomfort. Yet the components of the system, aside from the bracket, constitute available off-the-shelf items and the bracket itself is a simple molded plastic piece which can be made in quantity quite inexpensively. Therefore, the overall costs of making and using the system are kept to a minimum.

BRIEF DESCRIPTION OF THE DRAWING

For a fuller understanding of the nature and objects of the invention, reference should be had to the following detailed description, taken in connection with the accompanying drawing, in which.

DESCRIPTION OF THE PREFERRED EMBODIMENT

Figure 1:
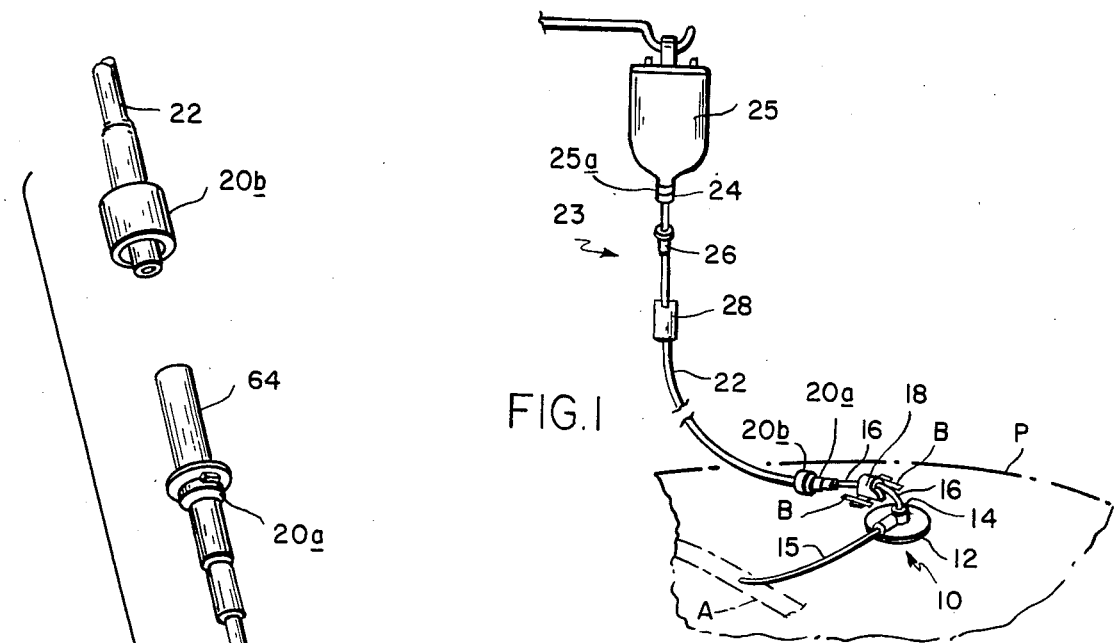
FIG. 1 is a diagrammatic view of the transcutaneous infusion system conducting infusate from a supply to an infusion site in a patient's body.

Referring to FIG. 1 of the drawing, the transcutaneous injection system is shown generally at 10 implanted in a patient P. The system includes an infusate injection port 12 implanted at a suitable location in the patient's body such as the peritoneal cavity. Injection port 12 has an entry 13 closed by a septum 14 situated directly under the patient's skin so that the injection port can be supplied with infusate by transcutaneous injection into the port through septum 14. A small diameter flexible tube 15 extends from the injection port to the infusion site in the patient illustrated herein as the carotid artery A.

A small-diameter flexible injection cannula 16 has one end projecting through the patient's skin and through the injection port's septum 14. Adjacent the injection site, the tube 16 engages around a bracket 18 secured to the patient's skin by adhesive strips B. The bracket is shaped and designed so that the flexible tube 16 makes a smooth transition from its perpendicular orientation at the injection site to a horizontal disposition adjacent that site. The opposite exposed end of tube 16 is terminated by a fitting or connector 20a. That connector is adapted to form a fluid-tight connection with a mating fitting or connector 20b mounted to the end of the tube 22 of a drug administration set indicated generally at 23. The opposite end of tube 22 carries a fitting 24 which is designed to connect to the outlet 25a of an elevated bag 25 containing a supply of infusate.

Preferably, the administration set 23 is of the type that includes a check valve 26 and a combined bacterial filter and air vent (I.F. filter) trap 28 in the fluid line between fitting 20b and bag 25. This permits the system to be separated from the infusate supply 25 by disconnecting fitting 24. When such disconnection is made, the valve 26 prevents infusate or blood from flowing out through system 10 due to the patient's arterial pressure. The combined air vent and bacterial filter 28 ensures that, when the reconnection is made to source 25, any bacteria and air bubbles that entered the fluid path at connection 24 are not passed through system 10 into the body. A suitable check valve for set 28 is disclosed in U.S. Pat. No. 4,286,628 and an appropriate I.V. filter is Gelman Type No. 6104420.

Figure 2:
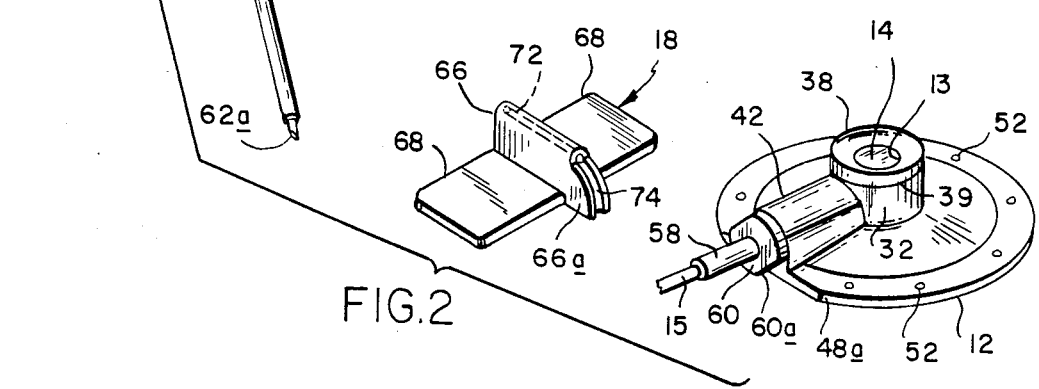
FIG. 2 is an exploded perspective view on a larger scale showing the components of the FIG. 1 system in greater detail.
Figure 3:
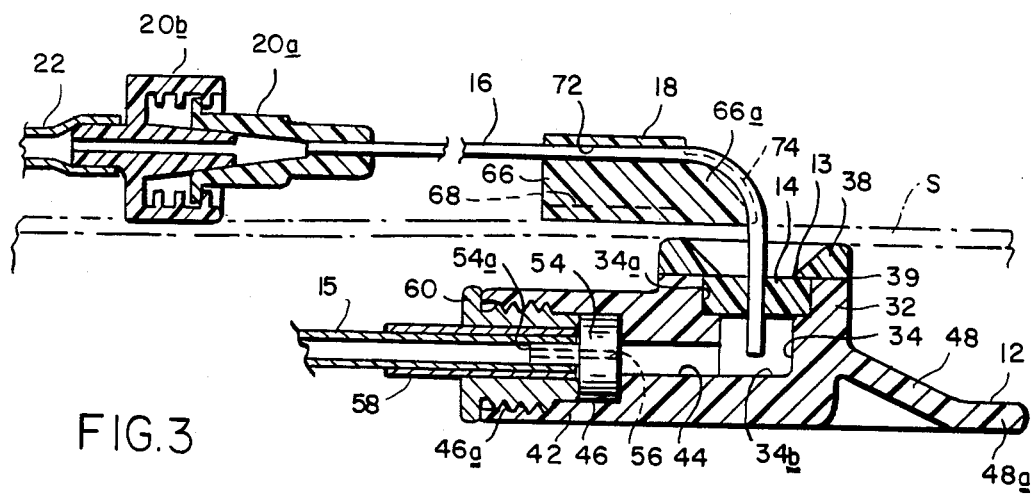
FIG. 3 is a sectional view on a still larger scale illustrating the operation of the FIG. 1 system.

Referring now to FIGS. 2 and 3, injection port 12 is machined from a suitable plastic compatible with the human system such as polytetrafluoroethylene. It comprises a central cylindrical section 32 having a relatively large diameter vertical passage or chamber 34 which is counterbored at 34a to seat the penetrable self-sealing septum 14. The septum is retained in place by a beveled ring 38 which is ultrasonically welded at 39 to the upper edge of section 32. The area of septum 14 inside ring 38 coincides with the entry 13 to the injection port 12.

Projecting laterally from section 32 is a barrel-shaped housing section 42 having a relatively small diameter axial passage 44 which intercepts passage 34. Passage 44 communicates with a relatively large diameter counterbore 46 in section 42 and an end segment of that counterbore is threaded at 46a. Passages 34 and 44 are not very large because it is not intended that they hold a large volume of infusate. Rather, they are simply conduits for conveying to outlet tube 15 the infusate injected under pressure into the passage 34 by the injection cannula that pierces septum 14.

The injection port is formed with a more or less circular dished flange section 48 which extends around the injection port section 32 extending to opposite sides of the barrel-shaped port section 42. The edge margin 48a of the flange is flattened so that it is more or less flush with the underside of injection port section 42 as best seen in FIG. 2 and small openings 52 are spaced around that margin for anchoring purposes.

The port's outlet tube 15 communicates with passage 44. For this, the adjacent end of the tube 15 is engaged over the stem 54a of a discoid resilient sealing member 54 which seats in bore 46. An axial passage 56 extends through the sealing member so that fluid can flow from passage 44 to and through tube 15. A reinforcing sleeve 58 surrounds the end segment of tube 15 and the tube and sealing member are held in place within bore 46 by a threaded annular screw 60 which engages around sleeve 58 and screws into the threaded segment of bore 46 so that it presses sealing member 54 against the end of the bore forming a fluid-tight seal therewith.

As seen in FIG. 2, flats 60a are formed on the screw head to aid in turning the screw. Thus, tube 15 and sealing member 54 can easily be removed and replaced with different such members in the event that the tube or seal is damaged or if it is desired to use a different diameter tube to achieve faster or slower fluid flow from the port to the infusion site.

When the injection port 12 is positioned at an appropriate location in the body with its septum 14 located directly under the skin as shown in FIG. 3, it can be retained in position by passing sutures through the openings 52 and through nearby body tissue.

Still referring to FIGS. 2 and 3, the injection cannula 16 is made of a thin-walled flexible resilient plastic material which is compatible with the human system, an example being polyethylene. A standard male Leur fitting 20a terminates one end of cannula 16 which fitting makes a bayonnet-type of connection with a mating fitting 20b attached to the end of tube 22 to establish a fluid-tight connection between the tube and the cannula.

The cannula 16 is designed to be used in conjunction with a long smaller-diameter pointed needle 62 which extends snugly through the cannula. A tubular handle 64 is attached to the upper end of needle 62 and, when the needle is fully seated in the cannula, the handle 64 engages against the upper end of fitting 20a while the pointed end 62a of the needle extends slightly beyond the end of cannula 16 as best seen in FIG. 2. Needle 16 can be solid or it can be hollow.

The relative diameters of the cannula 16 and needle 62 are such that the cannula engages snugly around the needle so that, when the pointed end of the needle 62a is inserted through the skin S and through injection port septum 14, the encircling sleeve 16 penetrates the septum along with the needle. The fit of the cannula about the needle is sufficiently tight and the cannula is sufficiently thin, yet stiff, that it is not wrinkled or pushed up along the needle as those two elements penetrate septum 14. The needle is pushed through the septum until it strikes the bottom wall 34b of the port passage 34. Thereupon, the needle 62 can be withdrawn from the septum leaving the cannula 16 in place within passage 34, its end being located slightly above wall 34b as shown in FIG. 3. After the needle is withdrawn, the cannula 16 is flexible enough so that it can be bent at right angles as shown in FIG. 3 so that its fitting 20a lies right against the patient's skin S.

Still referring to FIGS. 2 and 3, the bracket 18 performs two functions. First, it assures that the cannula 16 is not bent so sharply as to block the flow of fluid through the cannula. Secondly, the bracket provides means for anchoring the injection cannula and tubing to the patient's body so that those components do not become entangled in bedding and clothing.

The bracket is a simple molded plastic part having an upstanding fin 66 and a pair of tabs 68 extending laterally from opposite sides of the fin. The fin is formed with a nose portion 66a which extends from one end of the fin beyond the tabs. A lengthwise passage 72 extends along adjacent the upper edge of fin 66 and a groove 74 extends along the upper edge of nose 66a in line with the corresponding end of passage 66.

In use, before the cannula 16 with its needle 62 is inserted into the injection port, it is passed through the passage 72 in bracket 18 so that the nose portion 66a of the bracket faces the pointed end of the needle. Then the cannula and needle are pierced through septum 14 and the needle 62 is withdrawn leaving the cannula in place as aforesaid. Next, the bracket 18 is positioned with the end of its nose portion 66a located right at the location where the cannula penetrates the skin S as shown in FIG. 3 and the cannula 16 is pulled back through the bracket passage 72 so that the cannula seats snugly in the bracket groove 74. Finally, the bracket is secured to the body by engaging adhesive strips B over bracket tabs 68 as shown in FIG. 1.

Since the cannula 16 is completely flexible, the bracket can be positioned on the body anywhere around the injection site so that the cannula 16 and tubing 22 can extend from that site in any convenient direction to the infusate supply 25 (FIG. 1). Consequently, the present system ensures that the infusion site is quite neat and uncluttered and that the tubing, fittings, etc. at that location are all secured and present minimum inconvenience to the patient. After securement of bracket 18, the fitting 24 which is attached to tube 22 is connected to the outlet of bag 25 which is maintained at a height above the patient to develop the necessary infusion pressure and fitting 20b is attached to the lower end of tube 22 is connected to fitting 20a.

It will thus be seen that the objects set forth above, among those made apparent from the preceding description, are efficiently attained, and, since certain changes may be made in the above construction without departing from the scope of the invention, it is intended that all matter contained in the above description or shown in the accompanying drawing be interpreted as illustrative and not in a limiting sense.

It is also to be understood that the following claims are intended to cover all of the generic and specific features of the invention herein described.

What is claimed as new and desired to be secured by Letters Patent of the United States is:

1. A transcutaneous infusion system comprising
    A. an implantable infusate injection port including a housing and having a self-sealing injection septum leading into the port and an outlet tube leading from the port, said injection port being arranged to be implanted in a human or animal body with the septum located directly under the skin and the outlet tube leading to an infusion site in the body;
    B. an injection set including a flexible injection cannula and a fitting at one end of the cannula, the opposite end of the cannula being insertable through said septum into the port; and
    C. a cannula retaining bracket having opposite end segments which are generally perpendicular to one another and an intermediate segment which makes a curved transition between said two end segments, all of said segments lying in a common first plane, and tab means integral with said retaining means and extending in a second plane perpendicular to said first plane and having a flat undersurface so that, when the bracket is positioned with its tab means undersurface flush against the skin surface with said one end segment located adjacent to the injection site, the bracket retains said cannula in a gentle more or less right-angle bend with the cannula fitting held close to the skin surface.

2. The infusion system defined in claim 1 and further including means for adhering the tab means to the skin surface.

3. The system defined in claim 1 wherein said injection port also includes
    A. a tubular sealing member including a stem whose diameter is selected to engage snugly in the end of said outlet tube; and
    B. means for releasably connecting said sealing member to said housing in fluid connection with said port so that different diameter outlet tubes may be connected selectively to the port by appropriate selection of the sealing member stem diameter.

* * * * *